United States Patent [19]

Fox

[11] Patent Number: 5,496,623
[45] Date of Patent: Mar. 5, 1996

[54] NATURALLY FLAME RESISTANT COTTON FIBER

[75] Inventor: Sally V. Fox, Aguila, Ariz.

[73] Assignee: Natural Cotton Colours, Inc., Wickenburg, Ariz.

[21] Appl. No.: 187,620

[22] Filed: Jan. 28, 1994

[51] Int. Cl.$^6$ ..................................................... D04H 1/00
[52] U.S. Cl. ......................... 428/224; 428/364; 428/365; 800/DIG. 27; 139/420 B
[58] Field of Search ..................................... 428/224, 289, 428/361, 921, 364, 365; 8/127.1, 181, 584; 800/DIG. 27

[56] References Cited

U.S. PATENT DOCUMENTS

| | | | |
|---|---|---|---|
| 4,921,756 | 5/1990 | Tolbert et al. | 428/373 |
| 5,238,464 | 8/1993 | Johnson et al. | 8/127.1 |

OTHER PUBLICATIONS

Mehta, R. D., "Flammability of Metal–Cation–Exchanged Carboxyethylated Cottons", *Textile Research Journal*, vol. 44, No. 10, pp. 825–826 (Oct. 1974).
Smith, Betty F. et al., *"Textiles in Perspective"*, (Title Page, pp. v–vi), Prentice–Hall, Inc., Englewood Cliffs, N.J. (1982).
Poehlman, John Milton, *Breeding Field Crops*, 3rd Edition, Van Nostrand Reinhold, New York (1987).
Isaacs, Jack L., "The Oxygen Index Flammability Test", *J. Fire & Flammability*, vol. 1, pp. 36–44, (Jan. 1970).
Mitzner, Stanley, "Determination of Textile Finishes", *Analytical Methods for a Textile Laboratory*, Second Edition, AATCC Monograph Number 3, pp. 155–156 (1968).
Reinhardt, Robert M. et al., "The Nonaqueous Carboxymethylation of Cotton", *Textile Research Journal*, pp. 873–877 (Nov. 1957).

*Primary Examiner*—George F. Lesmes
*Assistant Examiner*—Kathleen L. Choi
*Attorney, Agent, or Firm*—Foley & Lardner

[57] ABSTRACT

Naturally flame resistant cotton fiber is provided. The naturally flame resistant cotton fiber of the present invention is used to produce fabric that complies with flammability safety regulations without application of a flame retardant chemical, or with application of reduced amounts of flame retardant chemical compared to fabric made from known cotton fiber. The flame resistant cotton fiber of the present invention can be used to produce articles of manufacture including garments, linens, mattresses and upholstery such as that used in home furnishings, motor vehicles and airplanes. Naturally flame resistant colored cotton fiber is provided that can be advantageously used to produce fabric and articles of manufacture that are not treated with chemical dyes or fire retardants. Cotton plant varieties that produce naturally flame resistant cotton fiber, as well as methods for the breeding and selection of these varieties, are provided.

5 Claims, No Drawings

NATURALLY FLAME RESISTANT COTTON FIBER

FIELD OF INVENTION

The present invention relates to naturally flame resistant cotton fiber, yarn and fabric. The naturally flame resistant cotton fiber and yarn of the present invention is used to produce fabric that complies with flammability safety regulations without application of a flame retardant chemical, or with application of reduced amounts of flame retardant chemical compared to fabric made from known cotton fiber. The present invention relates to naturally flame resistant cotton fiber that is used to produce articles of manufacture such as garments, linens, and upholstery for motor vehicles and airplanes. The present invention also relates to naturally flame resistant colored cotton fiber that can be used to produce articles of manufacture that are not treated with dyes or flame retardant chemicals. The present invention relates to cotton plant varieties that produce flame resistant cotton fiber, as well as methods for the breeding and selection of these varieties.

BACKGROUND OF THE INVENTION

Cotton is the world's most widely used textile fiber. The popularity of cotton can be attributed, in part, to the relative ease of cotton production compared to other fibers and the applicability of cotton fiber to a wide variety of textile products. For example, the majority of fabrics used in the garment and home furnishings industries are manufactured from cotton fiber. One of the reasons that cotton is a widely used textile in the apparel industry is that it is very comfortable to wear. Cotton fabric is comfortable to wear because this fiber has relatively high level of moisture absorption and good wicking properties.

One disadvantage of cotton fabric, however, is that it ignites easily and burns rapidly. The flammability of a fabric is dependent upon its composition. Mehta, R. D., *Textile Research Journal* 44(10): 825–826 (1974), incorporated herein by reference, for example, found that the extent of flame and glow resistance of a fabric increased as the carboxyl and metal contents of the fabric increased. In view of the danger posed by flammable textiles in general, the government has promulgated consumer safety regulations for textiles including safety standards for carpets and rugs, mattresses and children's sleepwear. The flammability characteristics of textiles used to manufacture upholstery found in motor vehicles and airplanes are also regulated by the government.

In order to reduce the inherent flammability of cotton fabrics, cotton fiber can be combined with inherently flame resistant fibers, such as synthetic fibers. For apparel use modacrylic fibers and matrix fibers of vinal/vinyon, among others, have been used. The resulting fabrics frequently lack the performance properties and consumer appeal of pure cotton fabric. Fiber composed of 50% vinal and 50% vinyon, for example, is not strong enough to form its own fabric and is not easily dyed. Another disadvantage of this method of producing fire resistant fabric is that yarns containing two or more fibers with different flammability characteristics tend to produce fabrics having non-uniform cross-sectional areas, and therefore, non-uniform fire resistant characteristics.

Alternatively, cotton fabric can be treated with flame retardant chemicals that change or interrupt the burning process known as pyrolysis. Cotton fabric treated with flame retardant chemicals, however, typically lack the performance properties and consumer appeal of pure cotton fabric.

During pyrolysis textile materials must first undergo decomposition to form volatile combustibles before they will burn. Decomposition occurs when the textile material is exposed to a sufficient source of heat. The decomposition temperature for textile materials is dependent upon the composition of the material and is different for different fibers. When the textile material decomposes, volatile materials are formed. The volatile materials ignite in the presence of oxygen to produce heat. The heat produced during pyrolysis may cause further decomposition of the textile material leading to its complete destruction.

The application of flame recardant chemicals may interrupt pyrolysis. For example, the flame retardant may be converted upon heating into acids and bases that catalyze decomposition of the textile at lower temperatures than are required for the formation of volatile combustibles. Compounds containing phosphorus are converted to acidic materials that catalyze the thermal decomposition of the polymer. Alternatively, the flame retardant may decompose or sublime upon heating to release large amounts of nonflammable vapors which exclude oxygen from the flame.

A need exists for a natural cotton fiber that is inherently flame resistant such that fabric made from the fiber complies with flammability safety regulations without application of flame retardant chemicals, or with application of reduced amounts of flame retardant chemical compared to fabric made from known cotton fiber. In addition, a need exists for a naturally colored cotton fiber that is inherently flame resistant such that fabric made from the fiber does not have to be treated with chemical dyes and fire retardants. A need exists for cotton varieties that produce flame resistant fiber and breeding methods for selection of cotton varieties that produce fiber that is inherently flame resistant.

SUMMARY OF THE INVENTION

The foregoing objects can be achieved by providing, according to one aspect of the present invention, cotton varieties that produce fiber that is naturally and inherently flame resistant. Fabric made from the naturally flame resistant cotton fiber of the present invention complies with flammability safety regulations without application of a flame retardant chemicals, or with application of reduced amounts of flame retardant chemical compared to fabric made from known cotton fiber.

Another aspect of the present invention relates to methods for breeding new cotton varieties that produce cotton fiber that is naturally flame resistant comprising the steps of crossing a first cotton plant that produces naturally flame resistant cotton fiber with a second cotton plant; planting seeds produced from said crossing; determining the level of flame resistance of the cotton fiber produced by progeny arising from said seeds; and selecting plants that produce flame resistant cotton fiber. The breeding method of the instant invention can be used to select cotton varieties that produce fiber that exhibits increased inherent flame resistance compared to either parent line. The first and second cotton plants of the breeding method of the instant invention can be any species of Gossypium including *G. barbadense* and *G. hirsutum*.

Another aspect of the present invention relates to fabric and articles of manufacture made from naturally flame resistant cotton fiber. The naturally flame resistant cotton fiber of the present invention, including naturally flame resistant colored cotton fiber, can be advantageously used to produce articles of manufacture such as garments, mattresses and upholstery, that are not treated with flame retardant chemicals, or are treated with lower amounts of flame retardant chemicals compared to fabric made from cotton fiber that is not inherently flame resistant.

Further objects, features, and advantages of the invention will become apparent form the detailed description of the invention which follows.

DESCRIPTION OF THE PREFERRED EMBODIMENT

As used herein, "flame resistant" is a property of a material whereby flaming combustion is prevented, terminated or inhibited, following application of a flaming or nonflaming source of ignition, with or without subsequent removal of the ignition source. Flame resistance can be an inherent or natural property of the basic material and is referred to as "inherently flame resistant" or "naturally flame resistant." Alternatively, flame resistance of a fabric can be imparted, or increased, by application of flame retardant chemicals or manufacture of yarn containing specific proportions of inherently fire resistant fibers.

As used herein, "fabric" includes any cloth comprised in whole, or in part, of cotton. The fabric may comprise only naturally flame resistant cotton fiber. On the other hand, the fabric may be a blend of the naturally flame resistant cotton fiber and any combination of synthetic fibers, animal fibers such wool or silk, bast fibers such as ramie or linen, leaf fibers such as abaca or agave, and seed fibers such as milkweed.

As used herein, "afterflame" is the time a specimen flames after removal of the ignition source and "afterglow" is the time the specimen glows after the flame is extinguished. "Char length" is the vertical length of the carbonized zone or area of burning of a specimen. "Count" in woven textiles is the number of warp yarns and filling yarns per inch as counted while the fabric is held under zero tension and is free of folds or wrinkles. As used herein, "articles of manufacture" include any object that is constructed in whole, or in part, with fabric that contains some amount of cotton fiber. "Cotton fiber" means seed lint, seed linters or both seed lint and linters. "Plain weave" is a weave consisting of yarns at right angles which alternately pass over and under each other. Each warp yarn interlaces with each filling yarn to form the maximum number of interlacing. "Twill weave" is a weave characterized by a series of floats staggered in a definite pattern in the warp direction. The yarns interlace in such as manner that dominant diagonal lines are observed. "Warp" is a yarn running lengthwise in a woven fabric while "fill" or "filling" are the crosswise yarns in a woven fabric.

As used herein, "naturally colored cottons" are cotton plants that produce fiber that is pigmented. Yarn and fabric produced from naturally colored cotton does not have to be dyed to produce a colored fabric. Naturally colored cottons offer several distinct advantages over white cottons. Naturally colored cottons can be worn by individuals that are allergic to the dyes and finishes typically used in the production of dyed cotton fabrics. Environmentalists are attracted to articles of manufacture produced from fabric composed of naturally colored cotton. The chemicals associated with the dyeing process are not needed during production of colored fabric made from naturally colored cotton. In addition, the cost of producing colored fabric from naturally colored cotton is less because the dyeing step is not necessary. The cotton varieties of the present invention produce fiber that is sufficiently long and strong to be machine spun. The fiber of the instant invention can be spun into yarns and made into fabrics using conventional methods such as those described in Smith et al., TEXTILES IN PERSPECTIVE, Prentice-Hall, Inc., Englewood Cliff, N.J. (1982), which is incorporated herein by reference.

A method for breeding new cotton varieties that produce cotton fiber that is naturally flame resistant is provided. A first cotton plant that produces naturally flame resistant cotton fiber is crossed with a second cotton plant, seeds from said cross are planted, and in the level of flame resistance exhibited by the cotton fiber produced by the progeny is determined. The first cotton plant can be any species of Gossypium including *G. hirsutum* and *G. barbadense*. Particularly preferred varieties for use as the first cotton plant in a method for breeding new cotton varieties that produce cotton fiber that is naturally flame resistant are 'Coyote' and 'Buffalo.'

Cotton varieties that have desirable agronomic characteristics, combined with production of naturally flame resistant fiber, are obtained by means of hybridization, backcrossing, mass selection or recurrent selection. Strategies for breeding and maintaining new cotton varieties are taught in J. M. Poehlman, BREEDING FIELD CROPS (3rd Ed.), Van Nostrand Reinhold, N.Y. (1987), which is incorporated herein by reference. New cotton varieties that produce fiber that is naturally flame resistant, or exhibit increased flame resistance compared to the parent, can be obtained using these breeding methods in combination with the step of screening for increased flame resistance.

Cotton plants that produce fiber that is naturally flame resistant can be identified by means of determining the oxygen index of fabric made from the fiber. For example, the oxygen index value for fabric manufactured from the fiber produced by one or more progeny of a given cross is analyzed. The oxygen index of a fabric is a good measure of relative flammability. The higher the oxygen index value the greater the flame resistance of the cotton fiber and fabric. Progeny that exhibit high oxygen index values are selected and incorporated into the breeding program.

Alternatively, the carboxyl group content for fiber produced by one or more progeny of a given cross can be determined and compared to the carboxyl group content of the fiber produced by the parents of the cross. The higher the carboxyl group content, the higher the flame and glow resistance of the fabric. Accordingly, progeny that produce fiber having a high carboxyl group content are selected and introduced into the breeding program.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLE 1

Breeding of the Cotton Varieties 'Coyote' and 'Buffalo' and Distinguishing Characteristics of Each Variety.

'Coyote' was bred in the following manner. In 1982 a collection of cotton seeds having fiber of superior quality and off-type color lint was made. Fiber quality was measured by determining the ease with which the fiber was spun by means of a spinning wheel. Seeds were planted in 1983.

The plants which matured displayed diverse phenotypes including different fiber colors and fiber quality.

Of those plants that matured in 1983, a single plant was selected that produced the highest quality lint within the reddish-brown color range. Seeds from this single plant selection were sown and thirty-five plants reached maturity. Of these, four plants produced white lint, twenty plants produced tan lint, and eleven produced reddish-brown lint.

In 1984 some 300 more seeds were planted from this same single plant selection of 1983 and nearly 100 plants reached maturity. Among these plants the ratio of white to tan to reddish-brown lint was 0 to 1 to 4, respectively. Plants producing reddish-brown lint were selected from among the plants that matured and the seeds from these plants were saved in bulk.

In 1985 the seeds collected in 1984 were planted and among the total number of plants that reached maturity, only 10% had tan lint and 2% had white lint. The remainder produced reddishbrown lint. Once again plants were selected that produced reddish-brown lint from among the plants that matured and the seeds produced by these plants were saved in bulk.

In 1986 the seeds collected in 1985 were planted and among the total number of plants that reached maturity, only 6% had tan lint and 2% had white lint. Plants producing reddish-brown lint from among the plants that matured in 1986 were selected and the seeds from these plants were saved in bulk.

'Coyote' is an upland cotton which most closely resembles Acala SJ2. American upland cotton is the type of *Gossypium hirsutum* predominantly grown in the United States. As compared to SJ2, 'Coyote' has improved seedling vigor and resistance to seedling diseases, improved resistance to insect pests, a more determinate and compact growth habit, different lint color and fiber quality. When grown in the San Joaquin Valley 'Coyote' closely resembles SJ2 with regard to flowering dates, flower morphology, boll size, boll shape, and yield of cottonseed and fiber. 'Coyote' exhibits improved seedling vigor and a more determinant growth habit compared to SJ2.

The lint color of 'Coyote' is distinctive. The is reddish-brown and has a color value at the center of the locule of RHS 165 C to D and at the outside of the boll of RHS 165 B to C. All color references were made to the Royal Horticultural Society (RHS) Colour Chart. 'Coyote' produces lint with a length, strength and micronaire of 0.97 inches, 23.0 g/tex and 4.7, respectively. The nitrogen and carboxyl group detemiations for 'Coyote' were 0.45% and 1.1%, respectively. In contrast, the nitrogen and carboxyl group detemiations for for white cotton were 0.13% and 0.16%, respectively. The higher flame resistance of the 'Coyote' cotton could be ascribed to the presence of the carboxyl groups.

'Buffalo' was bred in the following manner. An ancestor of 'Coyote,' designated A1, was used as the female parent in a cross to Pima S5 as the male parent in 1983. American Pima cotton is a type of *Gossypium barbadense*. In 1984 a single plant selection from the S5×A1 cross was made and designated H12. The plant H12 was selected because it had a *G. barbadense* phenotype but produced brown lint as well as smooth seeds. Seeds from H12 were collected and planted in 1985. A single plant selection was made in 1986 and designated S. The plant S was selected because it had a *G. barbadense* phenotype but produced brown cotton fiber. Seeds from S were collected and planted in 1987.

A single plant selection was made in 1987 and designated SF. Seeds from SF were collected and planted in 1988. A single plant selection was made in 1988 and designated 4T. Seeds from 4T were collected and planted in 1989. Bulk selections were made in 1990 through 1993 and off-type plants were rogued.

The resulting cotton variety 'Buffalo' (ATCC designation 97210) is stable and uniform. 'Buffalo' most closely resembles Pima S5 in plant growth, maturity, boll size and coloration of leaves and stems. 'Buffalo' produces smooth seeds. The major differences between 'Buffalo' and Pima S5 relate to the color and quality of the lint. 'Buffalo' produces lint that is bronze-brown in color with a color value of RHS 199A while Pima S5 produces white lint. The fiber length for 'Buffalo' is 1.06 to 1.10 inches while that for Pima S5 is 1.25 to 1.30 inches.

Another significant difference between 'Buffalo' and Pima S5 is that 'Buffalo' unlike Pima S5, produces fiber that is naturally flame resistant. The cross of 'Coyote' to Pima S5 to obtain a Pima-type cotton that produces cotton fiber that is inherently flame resistant demonstrates that the flame resistance can be predictably and reproducibly introgressed into diverse Gossypium genetic backgrounds.

EXAMPLE 2

Flame Resistant Characteristics of 'Coyote' and 'Buffalo' Cotton Fiber.

Oxygen Index

Oxygen index (OI) values were calculated to determine the lower limits of flammability. In this test, the oxygen level of an oxygen-nitrogen atmosphere was decreased until combustion of the specimen was barely sustained.

The 4 oz/sq yard 'Coyote' and 'Buffalo' fabric samples, untreated with flame retardant exhibited mean OI values in a range of 20–22, as shown in Table 1. The OI values for untreated pure cotton fabric of a similar weight known in the prior art range from 17 to 18, depending upon the construction of the fabric. Accordingly, fabric made from 'Coyote' and 'Buffalo' fiber is more flame resistant than pure cotton known in the prior art. Fabric made from 'Coyote' and 'Buffalo' fiber exhibited slightly higher OI values after one laundering.

Application of a 25% concentration of the flame retardant U6P to the 'Coyote' and 'Buffalo' 4 oz/sq yd fabric samples resulted in higher OI values of 34. After the fabric was laundered once, however, the OI values decreased.

TABLE 1

Mean Oxygen Index (percentage) for 4 oz/sq yd Fabrics at Designated Flame Retardant and Care Levels

| Fabric | 0% Flame Retardant OI Value | 25% Flame Retardant OI Value |
|---|---|---|
| 'Coyote' 0-L | 20 | 34 |
| 'Coyote' 1-L | 21 | 24 |
| 'Buffalo' 0-L | 21 | 34 |
| 'Buffalo' 1-L | 22 | 24 |

Key:
0-1 = Zero laundering
1-L = One laundering

Table 2 lists the OI values for the 10 oz/sq yd fabrics. The OI values for the 'Coyote' and 'Buffalo' fabrics treated with 0% flame retardant were in the range of 20–21 and therefore were similar to the OI values obtained with 4 oz/sq yd fabrics. The OI value for the 10 oz/sq yd fabric treated with 25% flame retardant was 36 and 35 for 'Coyote' and' 'Buffalo', respectively. The OI values for 10 oz/sq yd fabric of 'Coyote' and 'Buffalo' following one drycleaning decreased. The OI for untreated pure cotton fabric of the same weight known in the prior art is approximately 18. Accordingly, fabric made from 'Coyote' and 'Buffalo' fiber is more flame resistant than pure cotton known in the prior art.

TABLE 2

Mean Oxygen Index (percentage) for 10 oz/sq yd Fabrics at Designated Flame Retardant and Care Levels

| Fabric | 0% Flame Retardant OI Value | 25% Flame Retardant OI Value |
|---|---|---|
| 'Coyote' 0-D | 21 | 36 |
| 'Coyote' 1-D | 20 | 28 |
| 'Buffalo' 0-D | 21 | 35 |
| 'Buffalo' 1-D | 21 | 29 |

Key:
0-D = Zero drycleaning
1-D = One drycleaning

Motor Vehicle Safety Standard No. 302

The 10 oz/sq yd 'Coyote' and 'Buffalo' fabric samples were tested according to federal flammability standards for textile materials in passenger vehicles pursuant to the Motor Vehicle Safety Standard No. 302—Flammability of Interior Materials: Passenger Cars, Multipurpose Passenger Vehicles, Trucks and Buses. Table 3 shows the test results expressed as mean burn rate in inches/minute at 0% and 25% flame-retardant levels and before and after one drycleaning.

To pass the Motor Vehicle Safety Standard, a test specimen cannot burn or transmit a flame front across its surface at a rate of more than four inches per minute. No deviation from the standard is acceptable.

'Coyote' and 'Buffalo' fabric that was not treated with flame retardant passed the test requirements, both before and after one drycleaning. The 'Coyote' and 'Buffalo' fabrics burned, but at a rate of less than four inches/minute. The specimens were totally consumed during burning. The 'Coyote' and 'Buffalo' test specimens treated with 25% flame retardant did not ignite, whether drycleaned or not. Both the 'Coyote' and 'Buffalo' fabrics therefore passed the Motor Vehicle Safety Standard test.

TABLE 3

Motor Vehicle Safety Standard No. 302 -
Flammability of Interior Materials: Passenger Cars,
Multipurpose Passenger Vehicles, Trucks and Buses
Mean Burn Rate (inches/minute) for 10 oz/sq yd Fabrics
at Designated Flame-Retardant Flame and Care levels

| Fabric | 0% Flame Retardant Burn Rate | 25% Flame Retardant Burn Rate |
|---|---|---|
| 'Coyote' 0-D | 1.73[a] | 0[a] |
| 'Coyote' 1-D | 1.92[a] | 0[a] |
| 'Buffalo' 0-D | 1.77[a] | 0[a] |

TABLE 3-continued

Motor Vehicle Safety Standard No. 302 -
Flammability of Interior Materials: Passenger Cars,
Multipurpose Passenger Vehicles, Trucks and Buses
Mean Burn Rate (inches/minute) for 10 oz/sq yd Fabrics
at Designated Flame-Retardant Flame and Care levels

| Fabric | 0% Flame Retardant Burn Rate | 25% Flame Retardant Burn Rate |
|---|---|---|
| 'Buffalo' 1-D | 1.81[a] | 0[a] |

Key:
0-D = Zero drycleaning
1-D = One drycleaning
[a]Passed MVSS No 302 Standard Federal Aviation Administration Pursuant to the Federal Aviation Administration (FAA) 25.853, Appendix F, Part I—Airworthiness Standards: Transport Category Airplanes, 10 oz/sq yd fabric samples of 'Coyote' and 'Buffalo' were tested. The FAA standard specifies that material passing the test procedures must be self-extinguishing when tested vertically. The standard further states that the average burn length cannot exceed 8 inches and the average flame time after removal of the flame source cannot exceed 15 seconds. In addition, drippings from the test specimen cannot continue to flame for more than an average of 5 seconds after falling. The results of these tests are shown in Table 4.

Untreated 'Coyote' and 'Buffalo' fabric failed the test standard before and after drycleaning. The mean burn rates and flame times exceeded test requirements. Test specimens were totally consumed during burning and there were no drippings from the specimens.

The 'Coyote' and 'Buffalo' fabrics treated with 25% U6P, however, passed the test requirements before and after one drycleaning. 'Coyote' and 'Buffalo' specimens would not ignite before drycleaning at this level of flame retardant. Specimens exhibited a short char length due to the 12 second exposure time of the flame to the fabrics. Even though 'Coyote' and 'Buffalo' fabrics ignited after one drycleaning, the burn lengths and flame times were at acceptable levels. The sections of the specimens that did burn were not consumed but remained intact.

TABLE 4

Federal Aviation Administration 25.853, Appendix F, Part
I - Airworthiness Standards: Transport Category Airplanes
Mean Burn Length (inches) and Mean Flame Time
(seconds) for 10 oz/sq yd Fabrics at Designated
Flame-Retardant and Care Levels

| Fabric | 0% Flame Retardant | | 25% Retardant | |
|---|---|---|---|---|
| | Burn Length | Flame Time | Flame Burn Length | Flame Time |
| 'Coyote' 0-D | 12.00[a] | 35.56[a] | 2.84[b] | 0[b] |
| 'Coyote' 1-D | 12.00[a] | 39.53[a] | 4.03[b] | 3.26[b] |
| 'Buffalo' 0-D | 12.00[a] | 35.91[a] | 2.89[b] | 0[b] |
| 'Buffalo' 1-D | 12.00[a] | 40.43[a] | 5.74[b] | 8.80[b] |

Key:
0-D = Zero drycleaning

TABLE 4-continued

Federal Aviation Administration 25.853, Appendix F, Part
I - Airworthiness Standards: Transport Category Airplanes
Mean Burn Length (inches) and Mean Flame Time
(seconds) for 10 oz/sq yd Fabrics at Designated
Flame-Retardant and Care Levels

| Fabric | 0% Flame Retardant | | 25% Retardant | |
|---|---|---|---|---|
| | Burn Length | Flame Time | Flame Burn Length | Flame Time |

1-D = One drycleaning
[a]Failed FAA Standard
[b]Passed FAA Standard

MATERIALS AND METHODS

Preparation of Test Specimens

Yarns from 'Coyote' and 'Buffalo' cottons were spun using open-end spinning, and two weights of fabrics were made from each color of cotton, including a 4 oz/sq yd plain weave fabric representing an apparel weight and a 10 oz/sq yd twill weave fabric simulating an upholstery weight. The twill weave was selected for the heavier fabric because yarns can be spaced closely together and tightly packed. All four experimental fabrics were manufactured at the International Center for Textile Research and Development (ICTRD), Texas Tech University, Lubbock, Tex. A physical description of the fabrics is given in Table 5. Following weaving, the fabrics were desized and scoured in one operation to remove sizing and wax. Flammability tests were conducted on 4 oz/sq yd fabric before and after one laundering, while the 10 oz/sq yd fabrics were tested before and after one drycleaning.

The Motor Vehicle Safety Standard No. 302 test was done with a MVSS 302 Flame Tester for motor vehicles (horizontal tester) and a vertical flame test apparatus was used for the FAA 25.853 test. Oxygen Index was determined with a Michigan Chemical's Oxygen Index/Smoke Densitometer. All testing equipment was located at the ICTRD.

Laundering and Drycleaning Equipment

Equipment used for laundering 4 oz/sq yd fabrics was located at the ICTRD and included a Kenmore Heavy Duty 70 Series washing machine, Model No. 110.92273100, and a Kenmore Heavy Duty Soft Heat dryer, Model No. 110.96274100. Drycleaning was conducted by a commercial drycleaning establishment, using a Model No. 6-A Prosperity drycleaning machine.

Flammability Testing Procedure

Flammability testing was conducted with fabric that was treated with 0% or 25% U6P flame retardant. The U6P flame retardant was prepared by reacting 6 moles of urea with 1 mole of phosphoric acid (85% technical grade) in a stainless steel vessel with constant stirring. The mixture was gradually heated to 150° to 160° C. and maintained at that temperature for 30 minutes.

Fabrics were treated with a 25% concentration of U6P which was applied to 30-yard lengths of the 'Coyote' and 'Buffalo' fabrics. A 50% concentration of U6P, measured at 39.75° Twaddell, was diluted with an equal amount of water and 0,001 percent wetting agent to a 25% concentration, measuring 19.5° Twaddell. The flame retardant was thoroughly mixed in a large vat for approximately 20 minutes and then transferred to the padding machine. The 4 oz/sq yd and 10 oz/sq yd fabrics were passed through the solution at five yards per minute and at pressure settings of 2.2 and 1.2, respectively. The wet pickup was 76%.

TABLE 5

Physical Description of the Fabrics

| Fabric | Fabrication | Ounces Per Square Yard | Percent Fiber Content | Warp Yarn Size | Filling Yarn Size | Yarn Twists Per Inch | Count (epi* × ppi**) |
|---|---|---|---|---|---|---|---|
| Coyote brown | Plain | 4.09 | 100 Cotton | 18/1 | 18/1 | 20.4 | 61 × 43 |
| Coyote brown | 3/1 Twill | 10.39 | 100 Cotton | 8/1 | 8/1 | 13.6 | 63 × 49 |
| Buffalo brown | Plain | 4.12 | 100 Cotton | 18/1 | 18/1 | 20.4 | 61 × 43 |
| Buffalo brown | 3/1 Twill | 10.57 | 100 Cotton | 8/1 | 8/1 | 13.6 | 66 × 49 |

*ends per inch
**picks per inch
Ends = ways yarns (lengthwise)
Picks = filling yarns (crosswise)

Instrumentation

Finish Application Instruments

The U6P flame retardant was applied at the ICTRD using commercial equipment, including:
 (1) a padding machine for application of the finish,
 (2) the Fliessner Drum Dryer for drying, and
 (3) the Famatex Tenter for keeping the fabric open and fixed at a desired or preset width.

After the fabric with flame retardant finish was dried, the fabrics were cured in an Artos Single-pass Conveyor Dryer, located at Texas Dyeing and Finishing, Graham, Tex.

Flammability Testing Instruments

The 4 oz/sq yd fabrics were dried in the drum dryer at 125° C. at a speed of 12 yards/minute. The 10 oz/sq yd fabrics were dried at 155° C. at four yards/minute. Fabrics were then cured in a belt dryer fat 171° F. for 2 minutes, 15 seconds.

Table 6 describes the number and sizes of fabric specimens tested. The Motor Vehicle Safety Standard and Federal Aviation Airworthiness Standard were performed on 10 oz/sq yd fabrics to ascertain if federal standards were met for textile use in passenger vehicles and airplanes.

TABLE 6

Specimen Numbers, Sizes, and Minimum Requirements for Flammability Tests

| Flammability Test | Specimen Size (inch) | Number of Specimens* | Minimum Requirements |
|---|---|---|---|
| MVSS No. 302 | 4 × 14 | 5 | Specimen shall not burn, nor transmit a flame front across its surface, at a rate of more than 4"/minute. |
| FAA 25.853, Appendix F, Part I | 2 × 12 | 5 | Flame applied for 12 seconds and removed. Textiles must be self-extinguishing when tested vertically. Average burn length may not exceed 15 seconds. Drippings from specimen may not continue to flame for more than an average of 5 seconds after falling. |

*3 replications
Motor Vehicle Safety Standard (MVSS) No. 302: Flammability of Interior Materials - Passenger Cars, Multipurpose Passenger Vehicles, Trucks, and Buses.

Fifteen warp and fifteen filling specimens each of the two experimental 10 oz/sq yd fabrics of 'Coyote' and 'Buffalo' were prepared for testing in accordance with Motor Vehicle Safety Standard (MVSS) No. 302: Flammability of Interior Materials—Passenger Cars, Multipurpose Passenger Vehicles, Trucks, and Buses. Specimens were conditioned for 24 hours at 70° F.±2° F. and a relative humidity of 65%±2%, placed in containers, and taken to an unconditioned environment for testing.

Each specimen was mounted in a U-shaped frame with one end of the specimen even with the open end of the frame. The mounted specimen was placed in a horizontal position in the center of the cabinet. A Bunsen burner with a 1½ flame was moved to the open end of the specimen for 15 seconds and then removed. Timing of actual flame-time began when the flame reached a point 1½ inches from the open end of the specimen and ended when the flame reached a point 1½ inches from the clamped end of the specimen. The burn rate was then calculated using the following formula:

$$B = 60 \times \frac{D}{T},$$

where

B=burn rate in inches per minute,

D=length the flame travels in inches, and

T=time in seconds for the flame to travel D inches.

The direction (warp or filling) that provided the most adverse test results was reported and analyzed. Table 8 gives the requirements a textile material must meet to pass the MVSS standard.

Federal Aviation Administration (FAA)—Airworthiness Standards: Transport Category Airplanes, Part 25.853, Appendix F, Part I Fifteen specimens each of the experimental 10 oz/sq yd fabrics of Coyote and Buffalo were tested according to Federal Aviation Administration (FAA)—Airworthiness Standards: Transport Category Airplanes, Part 25.853, Appendix F, Part I. Specimens were conditioned to 70° F.±2° F. at a relative humidity of 65%±2% for 24 hours and were then individually moved in containers to an unconditioned environment for testing. This is a modification of the federal standard which requires a relative humidity of 50%±5% and a conditioned environment until specimens are subjected to the flame. Again, this change is a result of the physical arrangement and atmospheric situations maintained in the labs were specimens were conditioned and tested.

Each specimen was mounted in a U-shaped frame, which was then suspended vertically in a prescribed, enclosed cabinet. Specimens were exposed to a 1½ inch flame, with a temperature of 1550° F., supplied by a Bunsen burner, which was moved to the center of the lower edge of each specimen for 12 seconds and then removed. Flame time, burn length, and flame time of drippings were recorded.

To meet the FAA test standard, textiles must be self-extinguishing when tested vertically and must meet the minimum requirements as reported in Table 3.5. The direction of weave (warp or filling) corresponding to the most critical flammability conditions was reported and analyzed.

Oxygen Index

OI values were determined using Michigan Chemical's Oxygen Index/Smoke Densitometer. A total of 15 OI values were obtained for each specimen. OI measurements were made before and after application of U6P flame retardant and before and after laundering or drycleaning. Each fabric specimen, measuring 2 inches by 5½ inches, was clamped into the holder and placed vertically in the mounting brackets in the approximate center of a cylindrical column. The top of the specimen was at least four inches below the top of the column. A clear glass cylinder was placed over the column and the gas flow was initiated. The desired level of nitrogen gas was first set (either 100, 110, 120, 190, 200, or 210 cc/sec, depending upon fabric weight) using the stainless steel (lower ball) float. The oxygen gas level was set using the Pyrex (upper ball) float. The nitrogen-oxygen gas mixture was allowed to flow for 30 seconds to purge the system.

The specimen was ignited with the ignition flame so that the entire top of the specimen was burning. The concentration of oxygen in the gas mixture was too high if the specimen burned past the four-inch reference mark on the U-shaped holder and had to be reduced until the critical (lowest) oxygen concentration to support burning was determined. The oxygen concentration was too low if the specimen extinguished before reaching the four-inch reference mark.

The oxygen index was calculated for each of the 15 readings obtained using the following equation:

oxygen index percent=$(100 \times O_2)/(O_2+N_2)$, where $O_2$=volumetric flow of oxygen and $N_2$=volumetric flow of nitrogen.

The oxygen index flammability test has been shown by Issacs, J. L., *J. Fire & Flammability* 1:36 (1970), incorporated herein by reference, and others, to be a good measure of relative flammability. The higher the OI value the greater the flame resistance of the fiber and fabric.

Laundering

The 4 oz/sq yd fabrics of 'Coyote' and 'Buffalo' were tested for flame resistance at 0% and 25% flame-retardant levels after one laundering. Laundering was completed at the International Center for Textile Research and Development, Texas Tech University, using soft water.

A maximum fabric load of four pounds was placed in the washer and filled with 21.7 gallons of warm, water. Seventeen grams of laundry detergent (8.7% phosphorus) were added, and each load was washed on a normal cycle, providing a 10-minute wash and an approximate 5-minute rinse. All fabrics were dried on the timed-drying cycle for 50 minutes at high heat. Near the end of the 50-minute time period, the dryer automatically switched to low heat to prevent overdrying, followed by a 10-minute cool down.

Drycleaning

The 10 oz/sq yd fabrics of 'Coyote' and 'Buffalo' were tested at 0% and 25% flame-retardant levels after one drycleaning. Fabrics were drycleaned by a local, commercial drycleaning establishment, using perchlorethylene drycleaning solvent. Fabrics were cleaned for 13 minutes in the drycleaning solvent and then dried for 20 minutes under heat, followed by a 10-minute cool-down and a 5-minute fluff cycle.

Nitrogen and Carboxyl Group Determinations

Nitrogen was determined by means of the standard Kjeldahl procedure for total nitrogen such as described by Mitzner, S., Determination of Textile Finishes, pg. 155–157, incorporated herein by reference. Carboxyl groups were estimated by a back titration method such as described by Reinhardt et al., Textile Research Journal :873 (1957).

Desizing and Scouring

The fabric was desized and scoured simultaneously in a Vald Henrickson gig. The sizing to be removed was polyvinylalcohol. The desizing and scouring solution consisted of one gram per liter of Tergitol NP-9 non-ionic detergent (Union Carbide), 0.5 ml per liter of hydogen peroxide (50%) and 0.125 ml per liter of glacial acetic acid. The temperature of the solution in the gig was raised to 90° C. and six ends were run. The solution was then drained and the gig refilled with water. The temperature was again raised to 90° C. and six ends were run to remove the chemicals. The water was drained and the fabrics were rinsed in cold water.

What is claimed is:

1. Cotton fiber produced by the variety designated 'Buffalo' (ATCC 97210).

2. Yarn comprising said cotton fiber of claim 1.

3. Fabric comprising said cotton fiber of claim 2.

4. Articles of manufacture comprising said fabric of claim 3.

5. Articles of manufacture according to claim 4, wherein said articles of manufacture are selected from the group consisting of garments, mattresses and upholstery.

* * * * *